US008080524B2

(12) United States Patent
Bakala et al.

(10) Patent No.: US 8,080,524 B2
(45) Date of Patent: Dec. 20, 2011

(54) AGENT FOR SLOWING HAIR LOSS AND/OR STIMULATING HAIR GROWTH

(75) Inventors: Joanna Elzbieta Bakala, Paris (FR); Jérôme Bignon, Le val Saint Germain (FR); Jean-Yves Lallemand, Palaiseau (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 969 days.

(21) Appl. No.: 11/884,543

(22) PCT Filed: Feb. 16, 2006

(86) PCT No.: PCT/EP2006/060029
§ 371 (c)(1),
(2), (4) Date: Aug. 17, 2007

(87) PCT Pub. No.: WO2006/087363
PCT Pub. Date: Aug. 24, 2006

(65) Prior Publication Data

US 2009/0048182 A1 Feb. 19, 2009

(30) Foreign Application Priority Data

Feb. 18, 2005 (FR) ..................................... 05 01672

(51) Int. Cl.
*A61K 38/07* (2006.01)
*A61P 17/14* (2006.01)

(52) U.S. Cl. ..................................... 514/20.7; 514/21.9

(58) Field of Classification Search ......................... None
See application file for complete search history.

(56) References Cited

U.S. PATENT DOCUMENTS

2005/0239697 A1* 10/2005 Philp et al. ...................... 514/12

FOREIGN PATENT DOCUMENTS

| | | | |
|---|---|---|---|
| WO | WO 88/00594 | A1 | 1/1988 |
| WO | WO 97/28183 | A1 | 8/1997 |
| WO | WO 00/32620 | A1 | 6/2000 |
| WO | WO 02/24218 | A1 | 3/2002 |
| WO | WO 2005/010027 | A2 | 2/2005 |

OTHER PUBLICATIONS

Definition of radical from www.merriam-webster.com/dictionary/free%20radical, pp. 1-2. Accessed Mar. 30, 2009.*
Alopecia from Merck Manual, pp. 1-4. Accessed Jun. 12, 2007.*
Leshin L, Dermatologi Disorders in Down Syndrome from www.ds-health.com/derm.htm, pp. 1-3. Accessed Jun. 14, 2007.*
Hair Loss-Hair Loss Treatment for Male Pattern Baldness from www.webmds.us/hair-loss.html., pp. 1-4. Accessed Jun. 14, 2007.*
Hair Loss-Better Health Channel from betterhealthchaneel.vic.gov.au/bhcv2/bhcarticles.ns/pages/Hair_loss? Open, pp. 1-3. Accessed Jun. 14, 2007.*
Types of Hair Loss from www.pennhealth.com/hairtransplant/types.html, p. 1. Accessed Jun. 14, 2007.*
Frequently Asked Questions from www.naaf.org/requestinfo/faq.asp, pp. 1-7. Accessed Jun. 14, 2007.*

* cited by examiner

*Primary Examiner* — Julie Ha
(74) *Attorney, Agent, or Firm* — Foley & Lardner LLP

(57) ABSTRACT

The cosmetic use of at least one compound of formula (I) wherein: $A_1$ is the radical corresponding to D- or L-Ser; $A_2$ is the radical corresponding to D- or L-Asp or Glu; $A_3$ is the radical corresponding to D- or L-Lys, Arg or Orn; $A_4$ is the radical corresponding to D- or L-Pro; $R_1$, $R_2$, $R_3$ are such as defined in the claims, as agent for controlling hair loss.

(I)

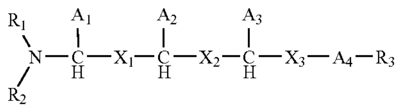

11 Claims, 9 Drawing Sheets

% variation in hair size control

Minoxidil $10^{-5}$ M

AcSDKP $10^{-10}$ M

Control

Minoxidil $10^{-5}$ M

AcSDKP $10^{-10}$M

AcSDKP $10^{-10}$ M

Control

Minoxidil $10^{-5}$ M

AcSDKP $10^{-10}$ M

Control

Minoxidil $10^{-5}$ M

AcSDKP $10^{-7}$ M

Control

Minoxidil $10^{-5}$ M

AcSDKP $10^{-10}$ M

AGENT FOR SLOWING HAIR LOSS AND/OR STIMULATING HAIR GROWTH

CROSS REFERENCE TO RELATED APPLICATIONS

This application is a National Stage application of PCT/EP2006/060029, filed Feb. 16, 2006, which claims priority from French patent application FR 0501672, filed Feb. 18, 2005.

Cosmetic use of at least one natural tetrapeptide Ac—N-Asp-Lys-Pro or one of its analogues as an agent for slowing down loss of hair and/or stimulating hair growth.

This invention concerns the cosmetic use in a composition of at least one tetrapeptide compound or analogue as an agent for slowing down loss of hair and/or stimulating hair growth.

Humans have around 150 000 hairs on their heads. Each hair consists of a shaft, the free part that emerges at the surface of the scalp, and a root (bulb) implanted in the hair follicle. Each hair has a lifespan ranging from 2 to 7 years.

Hair is produced by a complex organ, the hair follicle, consisting of a dermal compartment and an epithelial compartment. Each of these compartments is subdivided into functional sub-compartments. The follicles act a <<reservoir>> of stem cells capable of giving rise to all the cell lines needed to reconstitute the follicles, epidermis and sebaceous glands.

In humans, hair growth and renewal are determined mainly by the activity of hair follicle and the surrounding dermo-epidermal environment. A follicle is either in the growth phase (production of the hair shaft) in the course of which hair grows in length (anagenic phase) or at a stage where growth has stopped (telogenic phase). After the telogenesis phase and as a result of a neo-morphogenic process, the follicle is regenerated from the reservoir of stem cells and initiates a new anagenic phase. With normal hair which is constantly renewed, about 85% of follicles are in the growth phase, 2% in the resting phase and over 10% in the falling out phase.

Men and women usually lose 50 to 150 hairs a day. Nevertheless, these hairs are replaced by new growth as a function of the hair growth cycle. When hair loss becomes visible, this means that it is excessive (very much in excess of 150 hairs per day) or, more commonly, because hairs which fall out are replaced by finer hairs as is the case with individuals with androgenetic alopecia. In such cases, hair re-growth becomes thinner and thinner and rarer from one cycle to the next.

There are many causes of hair loss: diseases such as cancer or lupus, hormonal changes, stress, certain medications or food deficiencies. However, in the vast majority of cases, hair loss is of hereditary or hormonal origin. In women, hair loss begins after menopause in particular.

Depending on the root cause of baldness, hair can grow back more or less easily. There is no cure-all treatment and each case of hair loss is complex and has to be treated appropriately.

In the case of androgenetic loss, the main cause of baldness in both men and women, rapid and effective treatment is necessary. If nothing is done, gradual atrophy of the hair follicles and roots takes place as well as a decrease in hair diameter and alopecia develops. There is no curative treatment for androgenetic alopecia. It actually results from the hair follicle being over-sensitive to dihydrostestosterone (DHT) which shortens the capillary growth phase. Administration of oral antiandrogens such as Finasteride (PROPECIA®), which blocks the enzyme responsible for transforming testosterone into dihydrotestosterone in the hair follicles, reduces hair loss and activates re-growth. However, while many hopes were pinned on this product, it is contraindicated in women and recent warnings have been issued with regard to its use in men. In fact, the results of a clinical study suggest that there is a risk of developing a serious form of cancer of the prostate in patients taking this drug.

Minoxidil (ROGAINE®), another anti-hair loss preparation currently available on the market, is only useful at the start of alopecia. Its application to the scalp delays the end of the hair growth cycle, and therefore hair loss, but it does not reconstruct inactive follicles. Hair loss recommences a few weeks after stopping treatment.

There are also cosmetic products containing agents which confer volume on thinning hair. However, these agents do not stimulate growth. They can nonetheless give the impression of thicker hair since they coat the hair shaft and thus increase its diameter. These products only offer a temporary solution since they disappear each time hair is washed.

It would therefore be useful to provide the cosmetic or pharmaceutical industry with an effective product that is devoid of side effects to stimulate hair growth and/or prevent hair loss. Such a product would therefore reduce, and possibly even prevent, alopecia.

The Applicant has discovered a natural tetrapeptide and analogues that stimulate vital hair functions, in particular by activating epithelial stem cells, and therefore to achieve the desired objective. These derivatives also have the advantage of being obtained by peptide synthesis routes that are easy to implement and which are therefore not costly. Moreover, these compounds also have very low, and possibly even no, toxicity for the body.

The peptides or analogues used within the scope of this invention are derivatives with the basic structure Acetyl-Ser-Asp-Lys-Pro (AcSDKP). Their therapeutic properties are well-established (WO-88/00594 and WO-97/28183).

The Applicant has recently demonstrated their angiogenic properties (WO-02/24218).

No documents of the prior art describe or suggest that these compounds could have a cosmetic anti-hair loss effect nor that their use could lead to a positive effect in stimulating stem cells present in the hair follicles.

This invention therefore concerns the use of at least one compound of formula (I):

(I)

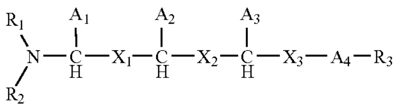

in which $A_1$ is the radical corresponding to D- or L-Ser, $A_2$ is the radical corresponding to D- or L-Asp or Glu, $A_3$ is the radical corresponding to D- or L-Lys, Arg or Orn, $A_4$ is the radical corresponding to D- or L-Pro, $R_1$ and $R_2$ are independently chosen from among the hydrogen atom, linear or branched substituted or non-substituted $C_1$-$C_{12}$ alkyl groups, substituted or non-substituted linear or branched substituted or non-substituted $C_7$-$C_{20}$ arylalkyl groups, $R_4CO$— and $R_4COO$— where $R_4$ is a linear or branched substituted or non-substituted $C_1$-$C_{12}$ alkyl group, or a substituted or non-substituted $C_7$-$C_{20}$ arylalkyl, where substitutions include OH, $NH_2$ and COOH, $X_1$ and $X_2$ are peptide or pseudopeptide bonds, $X_3$ is a radical chosen from among —CO and —$CH_2$—, and $R_3$ is a group chosen from among —OH, —$NH_2$, linear or branched alcoxy $C_1$-$C_{12}$ or —NH—$X_4$—$CH_2$—Z, where $X_4$ is a linear or branched $C_1$-$C_{12}$ hydrocarbon group and Z is a hydrogen atom or —OH, —$CO_2$H or —$CONH_2$, as well as their physiologically acceptable salts, in a composition as an agent for controlling hair loss.

Among the alkyl groups particularly suited to implementation of this invention, linear or branched $C_1$-$C_6$ alkyl groups are preferred. In particular, the methyl, ethyl, propyl, isopropyl, butyl, isobutyl and tertbutyl groups can be cited.

The term aryl group in the context of this invention relates to an aromatic carbon group with 6 to 14 carbon atoms. The phenyl, naphthyl and anthracenyl groups can be cited as examples of this.

The preferred arylalkyl groups of the invention include the benzyl and phenethyl groups.

The peptides or pseudopeptides corresponding to formula (I) are derived form the basic tetrapeptide structure Acetyl-Ser-Asp-Lys-Pro (AcSDKP) (SEQ ID NO: 1).

The term "radical corresponding to" refers to the radical A of formula:

$NH_2$—CH(A)-COOH corresponding to the amino acid.

Thus, A is:

—$CH_2$OH for Ser,

—$CH_2$COOH for Asp,

—$CH_2$—$CH_2$—COOH for Glu,

—$(CH_2)_3$—NH—C(NH)$NH_2$ for Arg,

—$(CH_2)_3$—$NH_2$ for Orn and

—$(CH_2)_4$—$NH_2$ for Lys for the terminal amino acid $A_4$, this consists of the structure:

=N—CH(A)-CO— or NH—(CH)A-CO—.

The term "pseudopeptide" refers to compounds that are similar to the reference peptide but in which one or more peptide —CO—NH— bonds have been replaced by a bond equivalent to the peptide bond called pseudopeptidic, that is —$CH_2$—NH—, —$CH_2$—S—, —$CH_2$—O—, —CO—$CH_2$—, —$CH_2$—CO—, —$CH_2$—$CH_2$— represented by $\psi(CH_2NH)$ for example.

Among the $R_1$ and $R_2$ radicals, the hydrogen atom or $R_4$CO— radicals are particularly preferred where $R_4$ represents a $C_1$-$C_3$ alkyl group, namely $CH_3$CO as well as HOOC—$CH_2$—$CH_2$—CO—O, Similarly, $R_3$ is preferably $NH_2$, OH or $NHCH_3$.

Among the compounds of formula (I) suited to implementation of the invention, the following can be cited:

$CH_3$CO-Ser-Asp-Lys-Pro-OH (SEQ ID NO: 1), $CH_3$CO-Ser-ψ-($CH_2$NH)-Asp-Lys-Pro-OH (SEQ ID NO: 2)

$CH_3$CO-Ser-Asp-ψ-($CH_2$NH)-Lys-Pro-OH (SEQ ID NO: 3)

$CH_3$CO-Ser-Asp-Lys-ψ-($CH_2$N)-Pro-OH (SEQ ID NO: 4)

$CH_3$CO-Ser-ψ-($CH_2$NH)-Asp-Lys-Pro-$NH_2$ (SEQ ID NO: 5)

$CH_3$CO-Ser-Asp-ψ-($CH_2$NH)-Lys-Pro-$NH_2$ (SEQ ID NO: 6)

$CH_3$CO-Ser-Asp-Lys-ψ-($CH_2$N)-Pro-$NH_2$ (SEQ ID NO: 7)

H-Ser-ψ-($CH_2$NH)-Asp-Lys-Pro-OH (SEQ ID NO: 8)

H-Ser-Asp-ψ-($CH_2$NH)-Lys-Pro-OH (SEQ ID NO: 9)

H-Ser-Asp-Lys-ψ-($CH_2$N)-Pro-OH (SEQ ID NO: 10)

$HOOCCH_2CH_2$CO-Ser-ψ-($CH_2$NH)-Asp-Lys-Pro-OH (SEQ ID NO: 11)

$HOOCCH_2CH_2$CO-Ser-Asp-ψ-($CH_2$NH)-Lys-Pro-OH (SEQ ID NO: 12)

$HOOCCH_2CH_2$CO-Ser-Asp-Lys-ψ-($CH_2$NH)-Pro-OH (SEQ ID NO: 13)

H-Ser-ψ-($CH_2$NH)-Asp-Lys-Pro-$NH_2$ (SEQ ID NO: 14)

H-Ser-Asp-ψ-($CH_2$NH)-Lys-Pro-$NH_2$ (SEQ ID NO: 15)

H-Ser-Asp-Lys-ψ-($CH_2$N)-Pro-$NH_2$ (SEQ ID NO: 16)

$HOOCCH_2CH_2$CO-Ser-ψ-($CH_2$NH)-Asp-Lys-Pro-$NH_2$ (SEQ ID NO: 17)

$HOOCCH_2CH_2$CO-Ser-Asp-ψ-($CH_2$NH)-Lys-Pro-$NH_2$ (SEQ ID NO: 18)

$HOOCCH_2CH_2$CO-Ser-Asp-Lys-ψ-($CH_2$N)-Pro-$NH_2$ (SEQ ID NO: 19)

$CH_3$CO-Ser-Asp-Lys-Pro-$NH_2$ (SEQ ID NO: 20)

H-Ser-Asp-Lys-Pro-$NH_2$ (SEQ ID NO: 21)

$CH_3$CO-Ser-Asp-Lys-Pro-$NHCH_3$ (SEQ ID NO: 22)

H-Ser-Asp-Lys-Pro-$NHCH_3$ (SEQ ID NO: 23)

$HOOCCH_2CH_2$CO-Ser-Asp-Lys-Pro-$NHCH_3$ (SEQ ID NO: 24)

$HOOCCH_2CH_2$CO-Ser-Asp-Lys-Pro-$NH_2$ (SEQ ID NO: 25)

A compound of formula (I) particularly suited to implementation of this invention is the natural tetrapeptide $CH_3$CO-Ser-Asp-Lys-Pro (AcSDKP) (SEQ ID NO: 1).

The term "physiologically acceptable salt" in the context of this invention refers to any salt prepared from any physiologically acceptable non-toxic acid, including organic and inorganic acids. Such acids include acetic, benzenesulphonic, benzoic, citric, ethanesulphonic, fumaric, gluconic, glutamic, hydrobromic, hydrochloric, lactic, maleic, malic, mandelic, methanesulphonic, mucic, nitric, pamoic, pantothenic, phosphoric, succinic, tartaric and paratoluenesulphonic acids. Advantageously, hydrochloric acid is used.

The compounds of formula (I) defined above have been shown to have a stimulating effect on cell growth and restructuring the epithelial sheath of hair follicles which constitute the source of stem cells. A large increase in the number of neo-keratinocytes and undifferentiated cells in the pilar structures of hair treated with compounds of formula (I) has been observed.

The Applicant has found that at the molecular level the effects of compounds used in accordance with the invention results in increased collagen IV and laminin 5 expression along the length of the hair, with a more pronounced effect in the median section situated between the bulge and the bulb.

One embodiment of the invention concerns the cosmetic use of a compound of formula (I) as defined earlier in a composition as an agent to trigger the growth and/or differentiation of stem cells and/or neo-keratinocytes in the epithelial sheath of hair and/or to stimulate the production of collagen IV and/or laminin 5 in the hair follicle.

More particularly, this invention concerns the cosmetic use of a compound of formula (I) as defined earlier in a composition as an agent to trigger and/or stimulate hair growth.

In another aspect of the invention, the compounds of formula (I) as defined above can be used to increase hair density.

Another particular aspect of the invention concerns the use of compounds of formula (I) as defined above in the prevention of alopecia.

The natural tetrapeptide $CH_3$CO-Ser-Asp-Lys-Pro (AcSDKP) (WO-88/00594) can be obtained by means of conventional peptide synthesis. The peptides or pseudopeptides of formula (I) related to the AcSDKP derivative can also be obtained by means of peptide or pseudopeptide synthesis as described in the document WO-97/28183.

The compounds of formula (I) are present in the compositions used to implement this invention in amounts ranging from 0.001% to 10% by weight, preferably between 0.005% and 5% by weight with respect to the total weight of the composition.

The cosmetic compositions used according to the invention are intended for topical use and can be in any pharmaceutical form conventionally used for this type of application, and namely in the form of emulsions (oil-in-water, water-in-oil, oil-in-water-in-oil or water-in-oil-in-water triple emulsions), aqueous gels, aqueous solutions, hydroalcoholic or oily solutions. They can be more or less fluid and in the form of a white or coloured cream, ointment, milk, lotion, serum, paste, mousse or biphase. They can also be in the form of an aerosol. The compositions used to implement this invention can be in the form of a lotion, gel, soap, aerosol, shampoo or mousse.

The compositions used within the scope of this invention contain derivatives contain, in addition to derivatives of formula (I), one or more excipients which can be chosen from among compounds with good compatibility with the active ingredients present in the formula. This can be, for example, natural polymers such as polysaccharides (xanthan gum, carob gum, peptin, etc.) or polypeptides, cellulose derivatives such as methylcellulose, hydroxypropylcellulose, hydroxypropylmethylcellulose, or synthetic polymers, polaxamers, carbomers, PVA or PVP.

Finally, the compositions of the invention can also contain various other excipients of the co-solvent type such as ethanol, glycerol, benzyl alcohol, wetting agents (glycerol), agents to facilitate diffusion (transcurol, urea) or even antibacterial preservatives (0.15% methyl p-hydroxybenzoate). They can also contain surfactants, stabilisers, emulsifiers, thickeners, other active ingredients generating a complementary effect or possibly synergetic effect, trace elements, essential oils, fragrances, colouring agents, collagen, chemical or mineral filters, hydrating agents or thermal spa waters.

In a particular embodiment of the invention, the derivatives of formula (I) are combined with at least one other active ingredient.

This invention also concerns a cosmetic process for the treatment and/or prevention of hair loss, particularly alopecia, consisting of the application to the scalp of a composition containing at least one derivative of formula (I) as defined earlier.

The following examples are given solely for the purpose of illustrating the invention and in no way limit it.

EXAMPLE 1

Experimental Study

Study of the stimulating activity of tetrapeptide AcSDKP on the growth of isolated hairs maintained in a state of ex vivo survival. This study was conducted on 66 human hair explants obtained from scalp-plasty.

Method

Hairs comprised of hair follicles were isolated by micro dissection and individually placed in wells (96-well culture plate) and maintained in survival for 15 days under conventional tissue culturing conditions (37° C., 5% $CO_2$) in Williams medium.

Tetrapeptide AcSDKP added to the culture medium was tested at three concentrations: $10^{-4}$ M, $10^{-7}$ M and $10^{-10}$ M. Minoxidil (2/1 diamino 6-piperidinopyrimidine 3-oxide) at a concentration of $10^{-5}$ M was used as a positive control.

Culture mediums containing the compounds to be tested were renewed every three days.

Hairs were photographed using a microscope and a CCD camera coupled to acquisition software and archiving.

Each hair was measured on D0, D3, D6, D8, D10, D13 and D15 using a LEICA IM1000 measurement module to give measurements in μm.

On D8 and D15 of treatment, six hairs from each batch (untreated control, Minoxidil, +AcSDKP $10^{-4}$ M, +AcSDKP $10^{-7}$ M, +AcSDKP $10^{-10}$ M) were removed and prepared for histological study.

Three explants from each batch were fixed in ordinary Bouin and the three other hairs were frozen and stored at −80° C.

In addition to measurements of the length of each hair, the general morphology of each hair was analysed and the expression of laminin 5 and collagen IV, two constituents of the basal membrane, was evaluated. Moreover, immunolabeling with anti-Ki67 antibodies (nuclear protein expressed in growing cells) was carried out of cells in mitosis in order to establish the mitotic index of follicle structures.

Results

1. Size of Hairs

Figure 1:
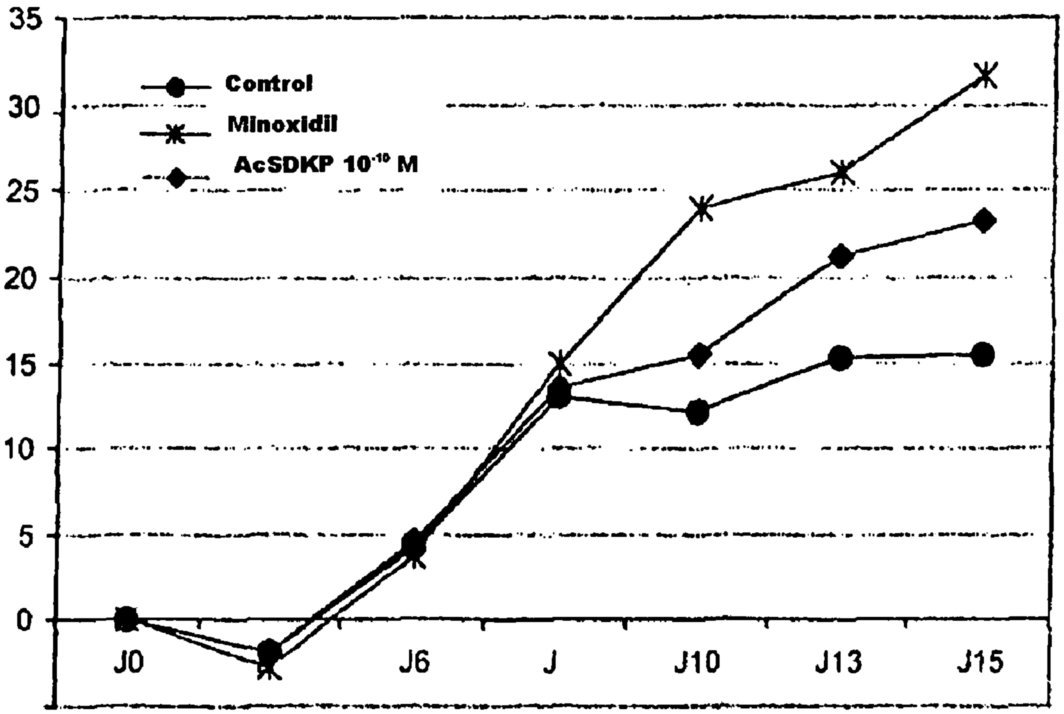
FIG. 1 : Evaluation of hair growth over 15 days following the treatment of hair explants with $10^{-10}$M AcSDKP, by comparison to a treatment with $10^{-5}$M Minoxidil and no treatment.

Each hair was photographed and its length evaluated using software giving values in μm. Observations made on D15 of treatment for the set of explants tested shows that the presence of AcSDKP at $10^{-10}$ M in the culture medium significantly stimulates hair growth (FIG. 1). On the other hand, no significant difference in the hair shafts was found in the presence of AcSDKP tested at higher concentrations.

2. Cell Proliferation

This study was conducted on cuts of frozen hairs. Immunolabelling of the cells present along the epithelial sheath with anti-Ki67 antibodies reveals a mitogenic effect of AcSDKP. The results presented in Table 1 show that AcSDKP at the three concentrations tested significantly increases the number of cells in mitosis in treated hair compared to control hair. Measurements on D8 of treatment show that this effect is maximal for AcSDKP at $10^{-10}$ M (+300%). Evaluation of the number of cells in mitosis also shows that the stimulating effect of AcSDKP is significantly greater than that found for Minoxidil at $10^{-5}$ M (+38%), especially at D8 of treatment.

The observations made with these hairs therefore demonstrate that AcSDKP ex vivo triggers cell proliferation more rapidly than Minoxidil in the external epithelial sheaths, regions where stem cells are located when hair is in the growth phase.

TABLE 1

| Average number of cells in mitosis per mm of hair | | | | | |
|---|---|---|---|---|---|
| Days | Control | Minoxidil ® $10^{-5}$ M | AcSDKP $10^{-4}$ M | AcSDKP $10^{-7}$ M | AcSDKP $10^{-10}$ M |
| D0 | 12.6 | | | | |
| D8 | 13.4 | 18.5 | 35.4 | 34 | 52.6 |
| D15 | 24.5 | 23.3 | 23.4 | 21.5 | 29.3 |

3. General Morphology

Analysis of the general morphology of histological cuts stained with Masson Trichromium focusing on the area between the opening of the sebaceous glands and the hair bulb.

Hairs cultured on D0 naturally undergo changes during survival as is observed after an in vivo graft. The restructuring effect of AcSDKP was visualised through the appearance of neo-keratinocytes along the conjunctival sheath which migrate from the bulge and to a lesser extent from the bulb, two regions where stem cells are found. Observation of the set of isolated hairs shows that the presence of AcSDKP in the culture medium leads to restructuring of the epithelial sheaths as of D8 of treatment. This effect leads to clear appearance of neo-keratinocytes along the length of the hair, from the epidermis to the bulb. The structure of the neo-keratinocytes formed in this way is uniform and stratified. It varies as a function of treatment time and AcSDKP concentration. The clearest activity was found on D15 of treatment with AcSDKP at $10^{-10}$ M.

Figure 2A:
FIG. 2A: Masson Trichomium staining of hair histological cuts at day 8 following a $10^{-10}$M AcSDKP treatment, a $10^{-5}$M Minoxidil treatment, and no treatment.
Figure 2A:
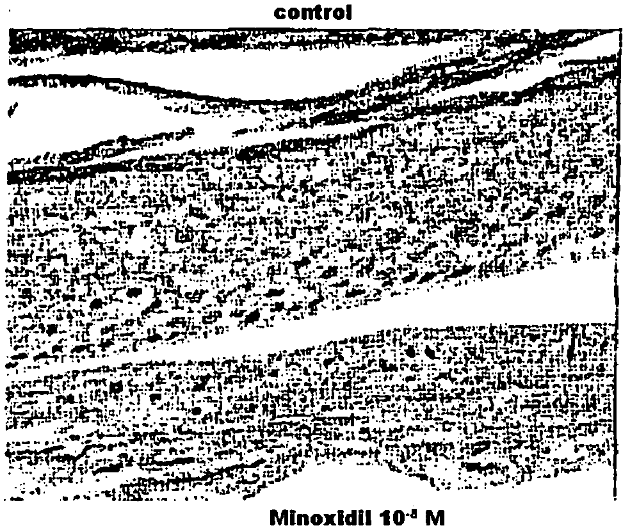
Figure 2A:
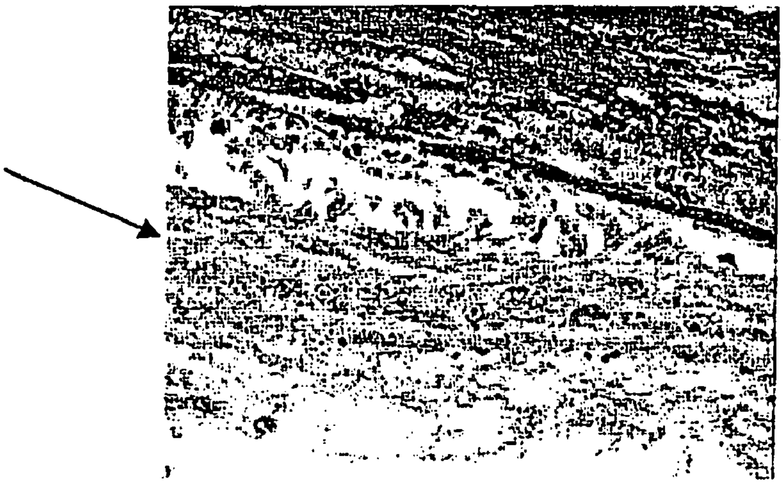

On D8, 2 to 3 neo-keratinocyte sites were visualised in the control hair but were absent from explants treated with Minoxidil at 10 μM as well as with AcSDKP $10^{-4}$ M. On the other hand, there was a very clear appearance of neo-keratinocytes (5 to 6 cell bases) throughout the length of hairs treated with AcSDKP at $10^{-7}$ M and $10^{-10}$ M. It should be pointed out that this epithelium adheres fully to the underlying collagen in hairs kept in survival in the presence of AcSDKP tested at the two active concentrations whereas the epithelial sheaths are more or less detached from collagen in the controls as well as in the presence of AcSDKP at $10^{-4}$ M and Minoxidil (FIG. 2A).

Figure 2B:
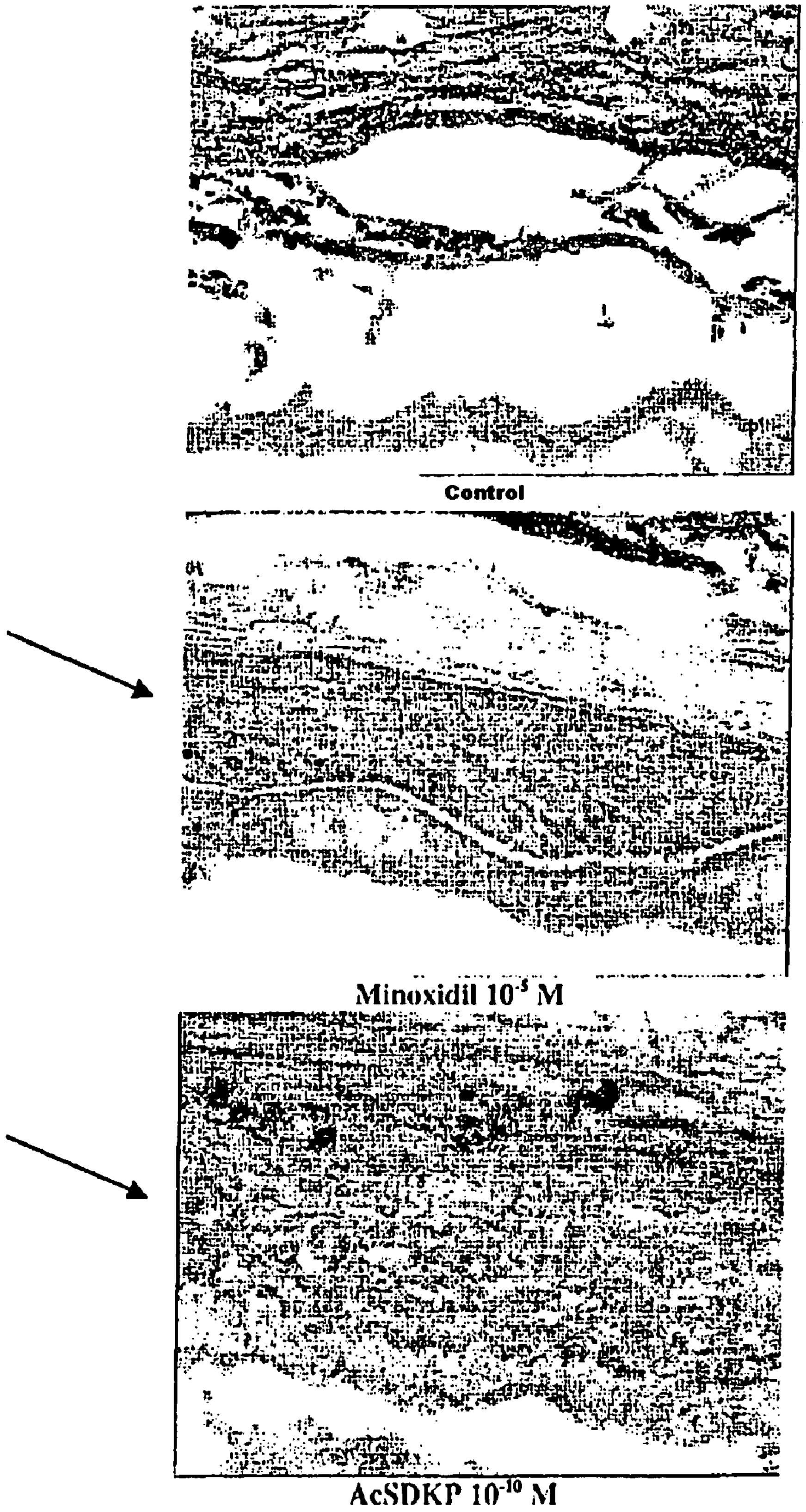
FIG. 2B: Masson Trichomium staining of hair histological cuts at day 15 following a $10^{-10}$M AcSDKP treatment, a $10^{-5}$M Minoxidil treatment, and no treatment.

On D15, neo-keratinocytes form a uniform and moderately stratified structure in treated hairs. This is slightly more structured with Minoxidil at $10^{-5}$ M compared to untreated hair. This becomes increasingly thicker with AcSDKP at $10^{-4}$ M, $10^{-7}$ M and especially with $10^{-10}$ M, with 6 to 7 cell bases close to the bulb, with up to 11 to 12 in the bulge (FIG. 2B).

4. Expression of Basal Membrane Collagen (Type IV)

Figure 3:
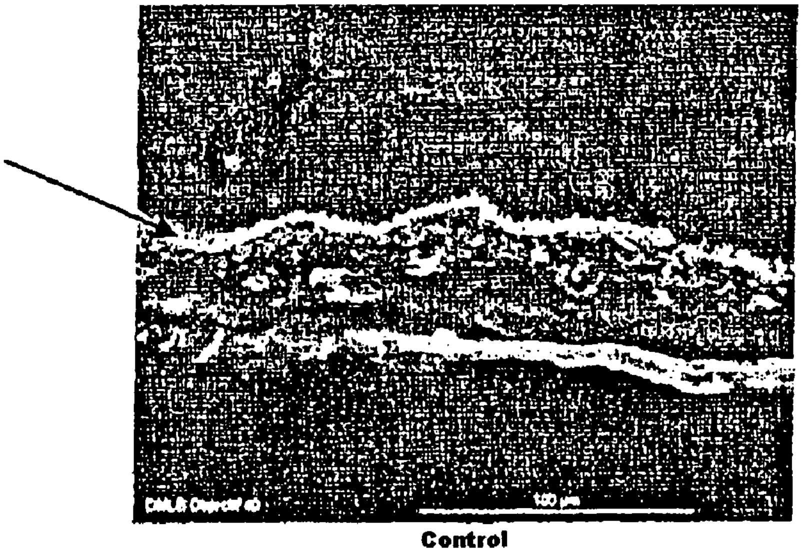
FIG. 3A: Immunolabelling of type IV collagen of hair histological cuts at day 8 following a $10^{-10}$M AcSDKP treatment, a $10^{-5}$M Minoxidil treatment, and no treatment.
FIG. 3B: Immunolabelling of type IV collagen of hair histological cuts at day 15 following a $10^{-10}$M AcSDKP treatment, a $10^{-5}$M Minoxidil treatment, and no treatment.
Figure 3:
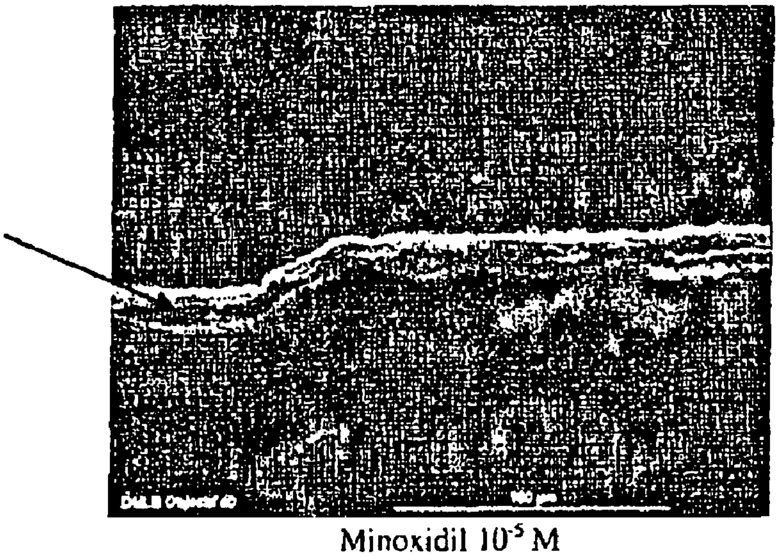
Figure 3:
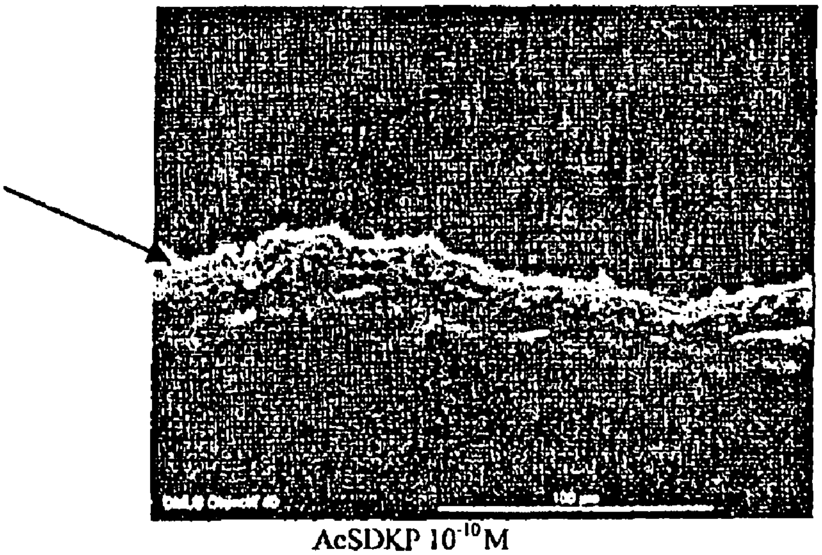
Figure 3B:
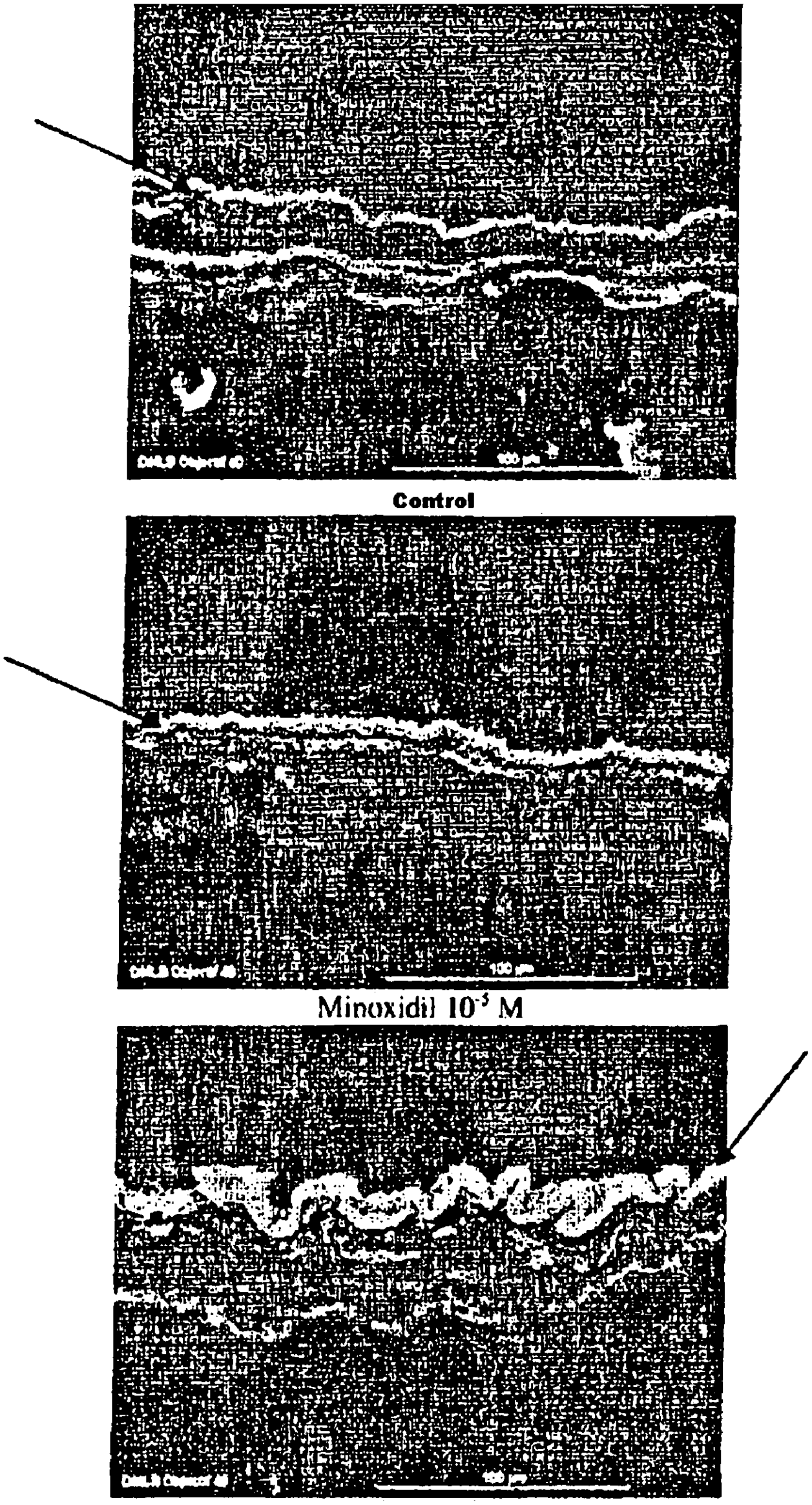

Immunolabelling of type IV collagen was carried out on frozen cuts of the control hairs and hairs treated with AcSDKP or Minoxidil in order to quantify this constituent of the basal membrane which separates the dermal compartment from the epithelial compartment. Analysis of the results obtained revealed a minimally stimulating effect of AcSDKP on expression of this protein in hair kept in survival in the presence of the tetrapeptide. In fact, as of D8 of treatment with AcSDKP at the three concentrations tested, there is a very clear increase in collagen IV in the bulb, and especially in the median section of hair at a point between the bulge and bulb. The increase in collagen levels found on D8 and D15 is all the more marked for AcSDKP tested at a concentration of $10^{-10}$ M. This expression of collagen IV is often less evident in hair treated with Minoxidil (FIGS. 3A and 3B).

5. Expression of Laminin 5

Figure 4A:
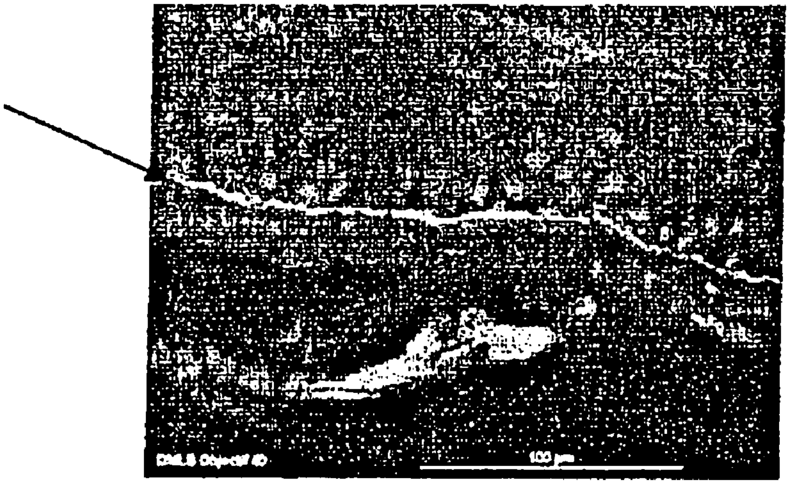
FIG. 4A: Immunolabelling of laminin 5 of hair histological cuts at day 8 following a $10^{-10}$M AcSDKP treatment, a $10^{-5}$M Minoxidil treatment, and no treatment.
Figure 4A:
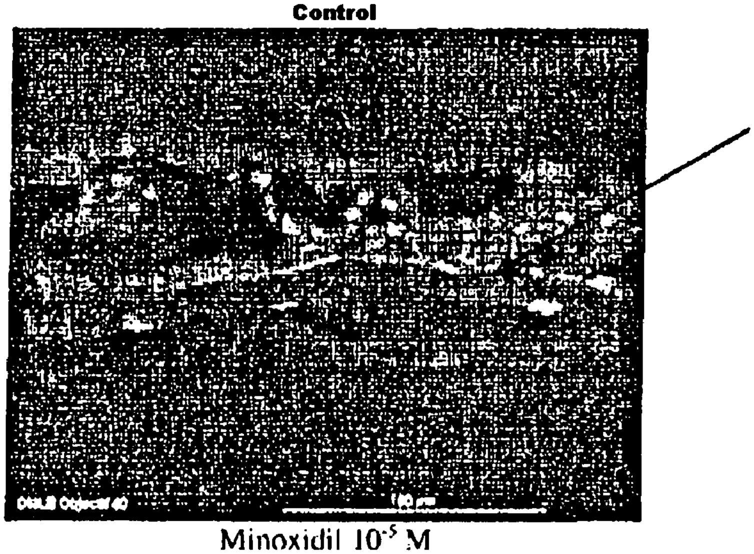
Figure 4A:
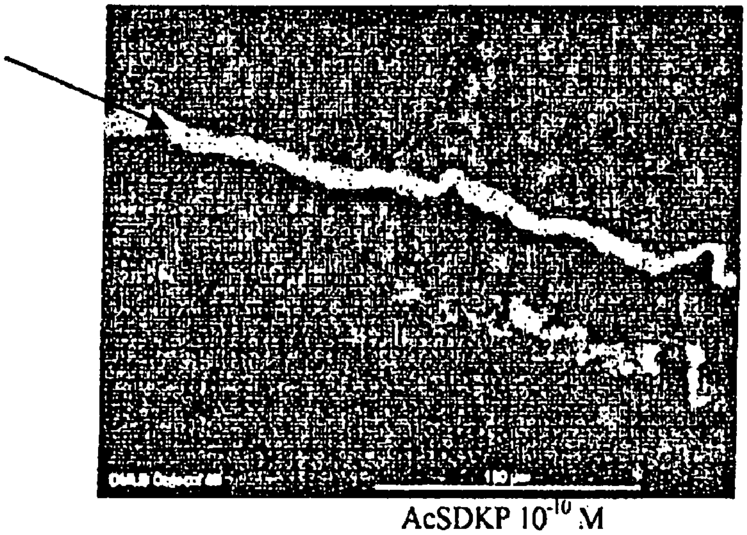
Figure 4B:
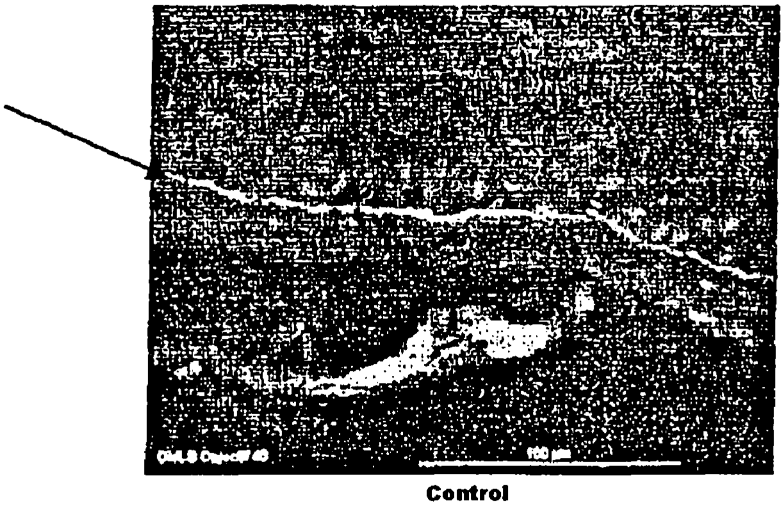
FIG. 4B: Immunolabelling of laminin 5 of hair histological cuts at day 15 following a $10^{-10}$M AcSDKP treatment, a $10^{-5}$M Minoxidil treatment, and no treatment.
Figure 4B:
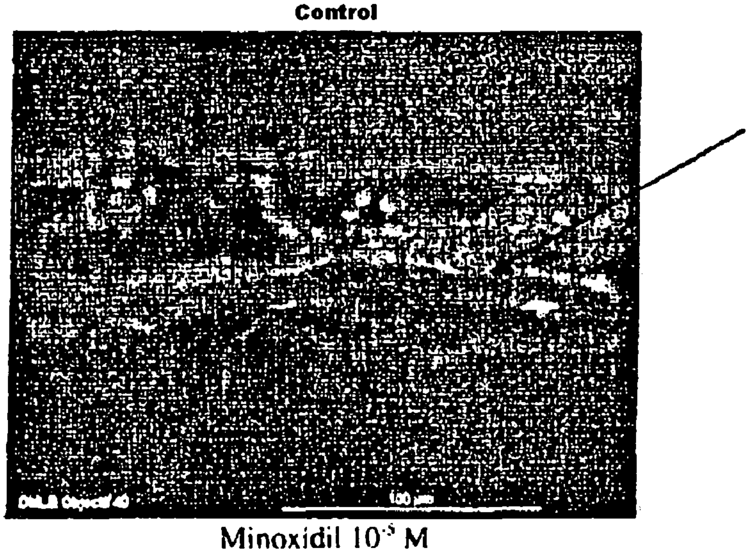
Figure 4B:
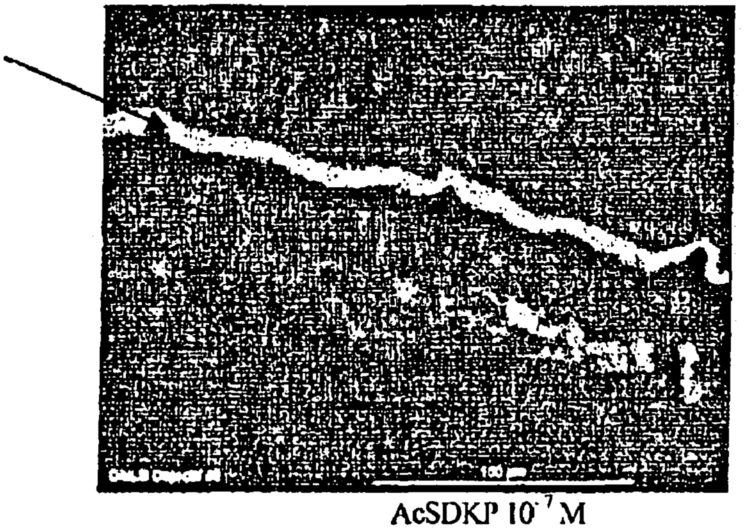

Laminin 5, another constituent of the basal membrane, is present in the bulb around the dermal papilla as well as in the median section of hair. Immunolabelling of laminin 5 revealed a significant increase in the level of this protein in hair structures following exposure of hair to AcSDKP. This effect was considerably more marked in the median zone of hair treated with AcSDKP at a concentration of $10^{-10}$ M (FIG. 4A) on D8 of treatment. Nevertheless, expression of laminin 5 was higher on D15 with AcSDKP at $10^{-7}$ M (FIG. 4B).

6. Expression of Keratin 19 (CK19), an Epithelial Stem Cell Marker

Figure 5:
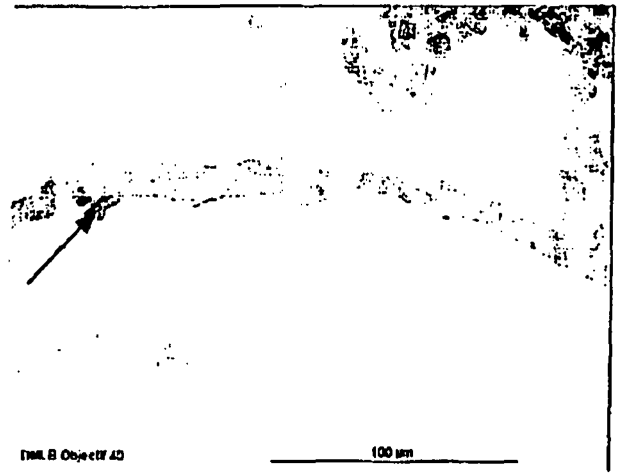
FIG. 5: Immunolabelling of keratin 19 of hair histological cuts following a $10^{-10}$M AcSDKP treatment, a $10^{-5}$M Minoxidil treatment, and no treatment.
Figure 5:
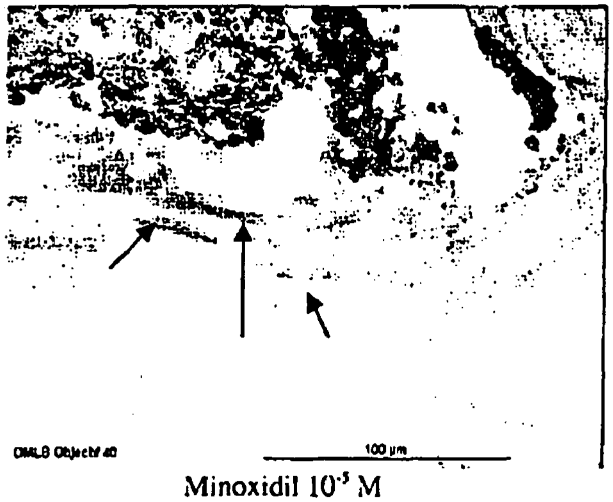
Figure 5:
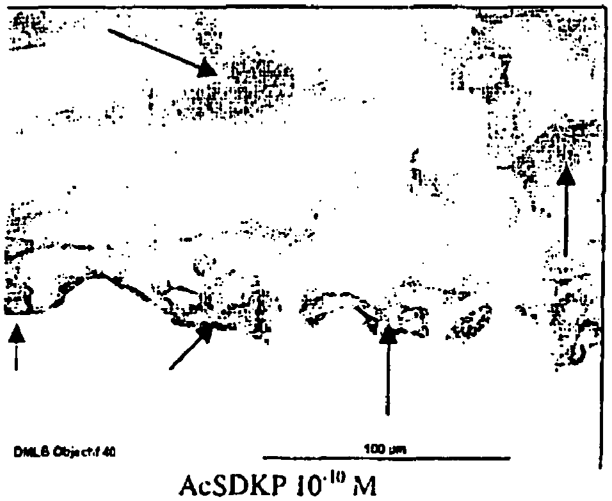

Immunolabeling of keratin 19 (CK19) was carried out on frozen cuts of control hairs and hairs treated with AcSDKP or Minoxidil in order to evaluate the proportion of undifferentiated primitive cells (or even stem cells) present in the external epithelial sheaths of the hair follicles. The results obtained show that expression of CK19 is significantly greater in hair kept in survival in the presence of the tetrapeptide compared to control hair and especially with respect to hair treated with Minoxidil. The increase in CK19 levels on D8 and D15 of treatment is maximal for AcSDKP tested at a concentration of 10.sup.-10 M (FIG. 5). Analysis of the results obtained shows a stimulating effect of AcSDKP in epithelial stem cells distributed along the external sheath of the follicle and responsible for renewal of the hair cycle.

Figure 6:
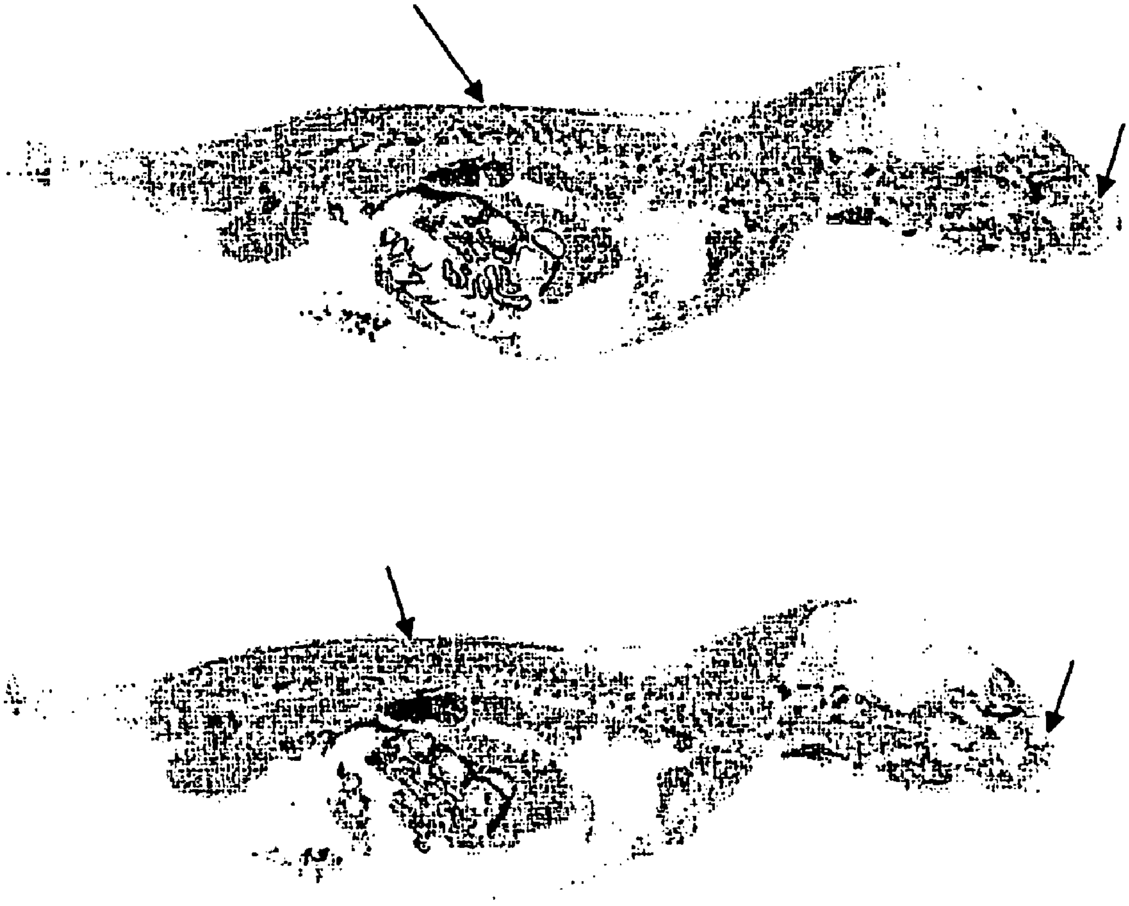
FIG. 6: In vivo radiolabelling of AcSDKP in rat following a $10^{-10}$M AcSDKP treatment, a $10^{-5}$M Minoxidil treatment, and no treatment.

7. Tissue Localisation of Radio Labelled AcSDKP in Animals Having Received a Single Dose In Vivo of the Tetrapeptide A complementary study using in vivo labelling of target organs of the peptide was carried out. This study was developed using $[^3H]$AcSDKP (100 Ci/mmole) specifically tritiated in the lysine lateral chain. In vivo injection of rats with $[^3H]$AcSDKP followed by autoradiography of cuts taken from the whole animal made it possible to visualise accumulation of the molecule in the animal's skin as well as in the hair follicles of whiskers (FIG. 6). This preferential site for AcSDKP suggests that the biological effect of this tetrapeptide is probably exerted in these areas.

EXAMPLE 2

Lotion

| | |
|---|---|
| Ethyl alcohol | 50% |
| AcSDKP | 0.1% |
| Water | 49.9% |
| Fragrance | q.s. |

EXAMPLE 3

Lotion

| | |
|---|---|
| Hydroxyethylcellulose | 0.4% |
| Ethyl alcohol | 25% |
| Butane 1,3-diol | 38.4% |
| Paramethylbenzoate | 0.2% |
| AcSDKP | 0.05% |

-continued

| | |
|---|---|
| Fragrance | 1% |
| Water | q.s. for 100% |

EXAMPLE 4

Oil-in-Water Emulsion

Oily Phase

| | |
|---|---|
| Vitamin E | 1% |
| Sorbitan monoleate | 2% |
| Quaternum-18 | 0.5% |
| Paraffin | 6.5% |

Aqueous Phase

| | |
|---|---|
| AcSDKP | 0.5% |
| Xanthan gum | 1% |
| Preservative | 0.3% |
| Fragrance | q.s. |
| Water | q.s. for 100% |

The invention claimed is:

1. A method for slowing down hair loss and/or stimulating hair growth, comprising applying to the scalp a composition comprising at least one compound of formula (I):

(I)

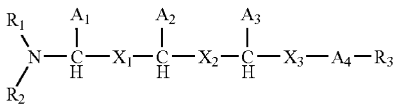

in which $A_1$ is $—CH_2OH$, $A_2$ is $—CH_2COOH$ or $—CH_2—CH_2—COOH$, $A_3$ is $—(CH_2)_4—NH_2$, $—(CH_2)_3—NH—C(NH)NH_2$, or $—(CH_2)_3—NH_2$, $A_4$ is

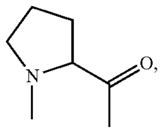

$R_1$ and $R_2$ are independently chosen from among the hydrogen atom, linear or branched substituted or non-substituted $C_1$-$C_{12}$ alkyl groups, substituted or non-substituted linear or branched substituted or non-substituted $C_7$-$C_{20}$ arylalkyl groups, $R_4CO—$ and $R_4COO—$ where $R_4$ is a linear or branched substituted or non-substituted $C_1$-$C_{12}$ alkyl group, or a substituted or non-substituted $C_7$-$C_{20}$ arylalkyl, where substitutions include OH, $NH_2$ and COOH, $X_1$ and $X_2$ are peptide or pseudopeptide bonds, $X_3$ is a radical chosen from among —CO and $—CH_2—$, and $R_3$ is a group chosen from among —OH, $—NH_2$, linear or branched alcoxy $C_1$-$C_{12}$ or $—NH—X_4—CH_2—Z$, where $X_4$ is a linear or branched $C_1$-$C_{12}$ hydrocarbon group and Z is a hydrogen atom or —OH, $—CO_2H$ or $—CONH_2$ as well as their physiologically acceptable salts.

2. The method of claim 1, wherein said compound stimulates the growth and/or differentiation of stem cells and/or neo-keratinocytes in the epithelial sheath of hair.

3. The method of claim 1, wherein said compound stimulates the production of collagen IV and/or laminin 5 in the hair follicle.

4. The method of claim 1, wherein said compound triggers and/or stimulates hair growth.

5. The method of claim 1, to increase hair density.

6. The method of claim 1, wherein the compound of formula (I) includes at least one pseudopeptide bond.

7. The method of claim 1, wherein the compound of formula (I) is chosen from among:

$CH_3CO$-Ser-Asp-Lys-Pro-OH (SEQ ID NO: 1), $CH_3CO$-Ser-ψ-($CH_2NH$)-Asp-Lys-Pro-OH (SEQ ID NO: 2)

$CH_3CO$-Ser-Asp-ψ-($CH_2NH$)-Lys-Pro-OH (SEQ ID NO: 3)

$CH_3CO$-Ser-Asp-Lys-ψ-($CH_2N$)-Pro-OH (SEQ ID NO: 4)

$CH_3CO$-Ser-ψ-($CH_2NH$)-Asp-Lys-Pro-$NH_2$ (SEQ ID NO: 5)

$CH_3CO$-Ser-Asp-ψ-($CH_2NH$)-Lys-Pro-$NH_2$ (SEQ ID NO: 6)

$CH_3CO$-Ser-Asp-Lys-ψ-($CH_2N$)-Pro-$NH_2$ (SEQ ID NO: 7)

H-Ser-ψ-($CH_2NH$)-Asp-Lys-Pro-OH (SEQ ID NO: 8)

H-Ser-Asp-ψ-($CH_2NH$)-Lys-Pro-OH (SEQ ID NO: 9)

H-Ser-Asp-Lys-ψ-($CH_2N$)-Pro-OH (SEQ ID NO: 10)

$HOOCCH_2CH_2CO$-Ser-ψ-($CH_2NH$)-Asp-Lys-Pro-OH (SEQ ID NO: 11)

$HOOCCH_2CH_2CO$-Ser-Asp-ψ-($CH_2NH$)-Lys-Pro-OH (SEQ ID NO: 12)

$HOOCCH_2CH_2CO$-Ser-Asp-Lys-ψ-($CH_2N$)-Pro-OH (SEQ ID NO: 13)

H-Ser-ψ-($CH_2NH$)-Asp-Lys-Pro-$NH_2$ (SEQ ID NO: 14)

H-Ser-Asp-ψ-($CH_2NH$)-Lys-Pro-$NH_2$ (SEQ ID NO: 15)

H-Ser-Asp-Lys-ψ-($CH_2N$)-Pro-$NH_2$ (SEQ ID NO: 16)

$HOOCCH_2CH_2CO$-Ser-ψ-($CH_2NH$)-Asp-Lys-Pro-$NH_2$ (SEQ ID NO: 17)

$HOOCCH_2CH_2CO$-Ser-Asp-ψ-($CH_2NH$)-Lys-Pro-$NH_2$ (SEQ ID NO: 18)

$HOOCCH_2CH_2CO$-Ser-Asp-Lys-ψ-($CH_2N$)-Pro-$NH_2$ (SEQ ID NO: 19)

$CH_3CO$-Ser-Asp-Lys-Pro-$NH_2$ (SEQ ID NO: 20)

H-Ser-Asp-Lys-Pro-$NH_2$ (SEQ ID NO: 21)

$CH_3CO$-Ser-Asp-Lys-Pro-$NHCH_3$ (SEQ ID NO: 22)

H-Ser-Asp-Lys-Pro-$NHCH_3$ (SEQ ID NO: 23)

$HOOCCH_2CH_2CO$-Ser-Asp-Lys-Pro-$NHCH_3$ (SEQ ID NO: 24)

$HOOCCH_2CH_2CO$-Ser-Asp-Lys-Pro-$NH_2$ (SEQ ID NO: 25).

8. The method of claim 1, wherein the compound of formula (I) is represented by the formula: $CH_3CO$-Ser-Asp-Lys-Pro-OH (SEQ ID NO:1).

9. The method of claim 1, wherein the compound of formula (I) is present in the composition in amounts ranging from 0.001% to 10% by weight.

10. A method for treating and/or preventing alopecia, comprising applying to the scalp a composition comprising at least one compound of formula (I):

(I)

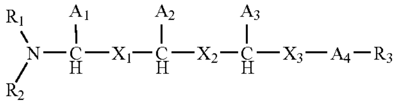

in which $A_1$ is $—CH_2OH$, $A_2$ is $—CH_2COOH$ or $—CH_2—CH_2—COOH$, $A_3$ is $—(CH_2)_4—NH_2$, $—(CH_2)_3—NH—C(NH)NH_2$, or $—(CH_2)_3—NH_2$,

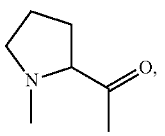

$A_4$ is $R_1$ and $R_2$ are independently chosen from among the hydrogen atom, linear or branched substituted or non-substituted $C_1$-$C_{12}$ alkyl groups, substituted or non-substituted linear or branched substituted or non-substituted $C_7$-$C_{20}$ arylalkyl groups, $R_4CO$— and $R_4COO$— where $R_4$ is a linear or branched substituted or non-substituted $C_1$-$C_{12}$ alkyl group, or a substituted or non-substituted $C_7$-$C_{20}$ arylalkyl, where substitutions include OH, $NH_2$ and COOH, $X_1$ and $X_2$ are peptide or pseudopeptide bonds, $X_3$ is a radical chosen from among —CO and —$CH_2$—, and $R_3$ is a group chosen from among —OH, —$NH_2$, linear or branched alcoxy $C_1$-$C_{12}$ or —NH—$X_4$—$CH_2$—Z, where $X_4$ is a linear or branched $C_1$-$C_{12}$ hydrocarbon group and Z is a hydrogen atom or —OH, —$CO_2H$ or —$CONH_2$ as well as their physiologically acceptable salts.

11. A method for increasing hair density, comprising applying to the scalp a composition comprising at least one compound of formula (I):

(I)

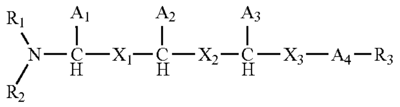

in which $A_1$ is —$CH_2OH$, $A_2$ is —$CH_2COOH$ or —$CH_2$—$CH_2$—COOH, $A_3$ is —$(CH_2)_4$—$NH_2$, —$(CH_2)_3$—NH—C(NH)$NH_2$, or —$(CH_2)_3$—$NH_2$,

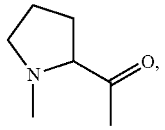

$A_4$ is $R_1$ and $R_2$ are independently chosen from among the hydrogen atom, linear or branched substituted or non-substituted $C_1$-$C_{12}$ alkyl groups, substituted or non-substituted linear or branched substituted or non-substituted $C_7$-$C_{20}$ arylalkyl groups, $R_4CO$— and $R_4COO$— where $R_4$ is a linear or branched substituted or non-substituted $C_1$-$C_{12}$ alkyl group, or a substituted or non-substituted $C_7$-$C_{20}$ arylalkyl, where substitutions include OH, $NH_2$ and COOH, $X_1$ and $X_2$ are peptide or pseudopeptide bonds, $X_3$ is a radical chosen from among —CO and —$CH_2$—, and $R_3$ is a group chosen from among —OH, —$NH_2$, linear or branched alcoxy $C_1$-$C_{12}$ or —NH—$X_4$—$CH_2$—Z, where $X_4$ is a linear or branched $C_1$-$C_{12}$ hydrocarbon group and Z is a hydrogen atom or —OH, —$CO_2H$ or —$CONH_2$ as well as their physiologically acceptable salts.

* * * * *

UNITED STATES PATENT AND TRADEMARK OFFICE

CERTIFICATE OF CORRECTION

PATENT NO. : 8,080,524 B2
APPLICATION NO. : 11/884543
DATED : December 20, 2011
INVENTOR(S) : Joanna Elzbieta Bakala et al.

It is certified that error appears in the above-identified patent and that said Letters Patent is hereby corrected as shown below:

IN THE CLAIMS

Column 24, Claim 10, line 41, please replace "A method for treating and/or preventing alopecia" with -- A method for treating alopecia --.

Signed and Sealed this
Seventeenth Day of April, 2012

David J. Kappos
*Director of the United States Patent and Trademark Office*

SEQUENCE LISTING

```
<160> NUMBER OF SEQ ID NOS: 25

<210> SEQ ID NO 1
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION

<400> SEQUENCE: 1

Ser Asp Lys Pro
1


<210> SEQ ID NO 2
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (1)..(2)
<223> OTHER INFORMATION: CH2NH bond

<400> SEQUENCE: 2

Ser Asp Lys Pro
1


<210> SEQ ID NO 3
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (2)..(3)
<223> OTHER INFORMATION: CH2NH bond

<400> SEQUENCE: 3
```

Ser Asp Lys Pro
1

<210> SEQ ID NO 4
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (3)..(4)
<223> OTHER INFORMATION: CH2N bond

<400> SEQUENCE: 4

Ser Asp Lys Pro
1

<210> SEQ ID NO 5
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (1)..(2)
<223> OTHER INFORMATION: CH2NH bond
<220> FEATURE:
<221> NAME/KEY: MOD_RES
<222> LOCATION: (4)..(4)
<223> OTHER INFORMATION: AMIDATION

<400> SEQUENCE: 5

Ser Asp Lys Pro
1

<210> SEQ ID NO 6
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (2)..(3)
<223> OTHER INFORMATION: CH2NH bond
<220> FEATURE:
<221> NAME/KEY: MOD_RES
<222> LOCATION: (4)..(4)
<223> OTHER INFORMATION: AMIDATION

<400> SEQUENCE: 6

Ser Asp Lys Pro
1

<210> SEQ ID NO 7
<211> LENGTH: 4
<212> TYPE: PRT
<213> ORGANISM: artificial

<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (3)..(4)
<223> OTHER INFORMATION: CH2N bond
<220> FEATURE:
<221> NAME/KEY: MOD_RES
<222> LOCATION: (4)..(4)
<223> OTHER INFORMATION: AMIDATION

<400> SEQUENCE: 7

Ser Asp Lys Pro
1

<210> SEQ ID NO 8
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: SITE
<222> LOCATION: (1)..(2)
<223> OTHER INFORMATION: CH2NH bond

<400> SEQUENCE: 8

Ser Asp Lys Pro
1

<210> SEQ ID NO 9
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: SITE
<222> LOCATION: (2)..(3)
<223> OTHER INFORMATION: CH2NH bond

<400> SEQUENCE: 9

Ser Asp Lys Pro
1

<210> SEQ ID NO 10
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: SITE
<222> LOCATION: (3)..(4)
<223> OTHER INFORMATION: CH2N bond

<400> SEQUENCE: 10

Ser Asp Lys Pro
1

<210> SEQ ID NO 11
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (1)..(2)
<223> OTHER INFORMATION: CH2NH bond

<400> SEQUENCE: 11

Ser Asp Lys Pro
1

<210> SEQ ID NO 12
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (2)..(3)
<223> OTHER INFORMATION: CH2NH bond

<400> SEQUENCE: 12

Ser Asp Lys Pro
1

<210> SEQ ID NO 13
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (3)..(4)
<223> OTHER INFORMATION: CH2NH bond

<400> SEQUENCE: 13

Ser Asp Lys Pro
1

<210> SEQ ID NO 14
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: SITE
<222> LOCATION: (1)..(2)
<223> OTHER INFORMATION: CH2NH bond
<220> FEATURE:
<221> NAME/KEY: MOD_RES
<222> LOCATION: (4)..(4)
<223> OTHER INFORMATION: AMIDATION

<400> SEQUENCE: 14

Ser Asp Lys Pro
1

<210> SEQ ID NO 15
<211> LENGTH: 4
<212> TYPE: PRT
<213> ORGANISM: artificial

<220> FEATURE:
<223> OTHER INFORMATION: AcSDKP tetrapeptide and analogues
<220> FEATURE:
<221> NAME/KEY: SITE
<222> LOCATION: (2)..(3)
<223> OTHER INFORMATION: CH2NH bond
<220> FEATURE:
<221> NAME/KEY: MOD_RES
<222> LOCATION: (4)..(4)
<223> OTHER INFORMATION: AMIDATION

<400> SEQUENCE: 15

Ser Asp Lys Pro
1

<210> SEQ ID NO 16
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: SITE
<222> LOCATION: (3)..(4)
<223> OTHER INFORMATION: CH2N bond
<220> FEATURE:
<221> NAME/KEY: MOD_RES
<222> LOCATION: (4)..(4)
<223> OTHER INFORMATION: AMIDATION

<400> SEQUENCE: 16

Ser Asp Lys Pro
1

<210> SEQ ID NO 17
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (1)..(2)
<223> OTHER INFORMATION: CH2NH bond
<220> FEATURE:
<221> NAME/KEY: MOD_RES
<222> LOCATION: (4)..(4)
<223> OTHER INFORMATION: AMIDATION

<400> SEQUENCE: 17

Ser Asp Lys Pro
1

<210> SEQ ID NO 18
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (2)..(3)
<223> OTHER INFORMATION: CH2NH bond
<220> FEATURE:
<221> NAME/KEY: MOD_RES
<222> LOCATION: (4)..(4)

-continued

<223> OTHER INFORMATION: AMIDATION

<400> SEQUENCE: 18

Ser Asp Lys Pro
1

<210> SEQ ID NO 19
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: SITE
<222> LOCATION: (3)..(4)
<223> OTHER INFORMATION: CH2N bond
<220> FEATURE:
<221> NAME/KEY: MOD_RES
<222> LOCATION: (4)..(4)
<223> OTHER INFORMATION: AMIDATION

<400> SEQUENCE: 19

Ser Asp Lys Pro
1

<210> SEQ ID NO 20
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 20

Ser Asp Lys Pro
1

<210> SEQ ID NO 21
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (4)..(4)
<223> OTHER INFORMATION: AMIDATION

<400> SEQUENCE: 21

Ser Asp Lys Pro
1

<210> SEQ ID NO 22
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)

<223> OTHER INFORMATION: ACETYLATION
<220> FEATURE:
<221> NAME/KEY: MOD_RES
<222> LOCATION: (4)..(4)
<223> OTHER INFORMATION: NHCH3

<400> SEQUENCE: 22

Ser Asp Lys Pro
1

<210> SEQ ID NO 23
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (4)..(4)
<223> OTHER INFORMATION: NHCH3

<400> SEQUENCE: 23

Ser Asp Lys Pro
1

<210> SEQ ID NO 24
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: MOD_RES
<222> LOCATION: (4)..(4)
<223> OTHER INFORMATION: NHCH3

<400> SEQUENCE: 24

Ser Asp Lys Pro
1

<210> SEQ ID NO 25
<211> LENGTH: 4
<212> TYPE: PRT
<213> ORGANISM: artificial
<220> FEATURE:
<223> OTHER INFORMATION: AcSDKP tetrapeptide and analogues
<220> FEATURE:
<221> NAME/KEY: MOD_RES
<222> LOCATION: (1)..(1)
<223> OTHER INFORMATION: COCH2CH2COOH
<220> FEATURE:
<221> NAME/KEY: MOD_RES
<222> LOCATION: (4)..(4)
<223> OTHER INFORMATION: AMIDATION

<400> SEQUENCE: 25

Ser Asp Lys Pro
1